US010092218B2

United States Patent
Li et al.

(10) Patent No.: US 10,092,218 B2
(45) Date of Patent: Oct. 9, 2018

(54) PELVIC DIGITIZER DEVICE WITH INERTIAL SENSOR UNIT AND METHOD

(71) Applicant: ORTHOSOFT, INC., Montreal (CA)

(72) Inventors: Di Li, Montreal (CA); Louis-Philippe Amiot, Hampstead (CA); Don Dye, Warsaw, IN (US); Myriam Valin, Laval (CA); Isabelle Robitaille, Montreal (CA); Francois Paradis, Boucherville (CA); Karine Duval, Montreal (CA); Yonik Breton, Montreal (CA); Simon Ferron-Forget, Montreal (CA)

(73) Assignee: ORTHOSOFT, INC., Montreal (CA)

( * ) Notice: Subject to any disclaimer, the term of this patent is extended or adjusted under 35 U.S.C. 154(b) by 69 days.

(21) Appl. No.: 13/954,288

(22) Filed: Jul. 30, 2013

(65) Prior Publication Data

US 2014/0031722 A1    Jan. 30, 2014

Related U.S. Application Data

(60) Provisional application No. 61/677,104, filed on Jul. 30, 2012.

(51) Int. Cl.
*A61B 5/107* (2006.01)
*A61F 2/46* (2006.01)
*A61B 34/20* (2016.01)

(52) U.S. Cl.
CPC .......... *A61B 5/1077* (2013.01); *A61F 2/4609* (2013.01); *A61B 2034/2048* (2016.02); *A61F 2002/4668* (2013.01)

(58) Field of Classification Search
CPC .. A61F 2/4609; A61F 2/34; A61F 2002/4623; A61B 5/45; A61B 5/4571;
(Continued)

(56) References Cited

U.S. PATENT DOCUMENTS 7,559,931 B2 * 7/2009 Stone .............................. 606/91
2004/0230199 A1   11/2004 Jansen et al.
(Continued)

FOREIGN PATENT DOCUMENTS

CN           1512857 A        7/2004
WO        2010030809 A1       3/2010
(Continued)

OTHER PUBLICATIONS

Ren, et al. "Investigation of navigation and robotic system for computer assisted orthopedic surgery: State-of-art and preliminary results." International Journal of Information Acquisition 6.03 (2009): 171-179. Retrieved from <http://www.bioeng.nus.edu.sg/biomm/pdfs/rn09ijiaCAOS.pdf> on Jan. 6, 2015.*

(Continued)

*Primary Examiner* — David J McCrosky
(74) *Attorney, Agent, or Firm* — Norton Rose Fulbright Canada LLP

(57) ABSTRACT

A pelvic digitizer device has a body defined by a shaft having a tooling end and a handle end with a handle for being manipulated. A visual guide is oriented in a reference plane of the digitizer device. A cup is connected to the tooling end and adapted to be received in an acetabulum of a patient. An inertial sensor unit is connected to the body, the inertial sensor unit having a preset orientation aligned with the reference plane.

19 Claims, 4 Drawing Sheets

(58) Field of Classification Search
CPC ....... A61B 5/4504; A61B 5/103; A61B 5/107; A61B 5/1071; A61B 5/1072; A61B 90/10; A61B 90/11; A61B 90/13; A61B 2034/101–2034/107; A61B 2034/2048; A61B 34/10
USPC .............................................. 600/587; 606/91
See application file for complete search history.

(56) References Cited

U.S. PATENT DOCUMENTS

| | | | |
|---|---|---|---|
| 2005/0148843 A1* | 7/2005 | Roose | 600/407 |
| 2005/0149050 A1 | 7/2005 | Stifter | |
| 2008/0051910 A1 | 2/2008 | Kammerzell | |
| 2008/0269757 A1 | 10/2008 | McMinn | |
| 2009/0099665 A1* | 4/2009 | Taylor | A61F 2/34 606/91 |
| 2010/0137871 A1* | 6/2010 | Borja | 606/91 |
| 2011/0060339 A1* | 3/2011 | de Wekker | 606/80 |
| 2011/0093086 A1 | 4/2011 | Witt | |
| 2011/0152871 A1 | 6/2011 | Park | |
| 2011/0218458 A1* | 9/2011 | Valin et al. | 600/595 |
| 2012/0157887 A1* | 6/2012 | Fanson | A61F 2/32 600/595 |
| 2012/0203140 A1* | 8/2012 | Malchau | A61B 5/1114 600/587 |

FOREIGN PATENT DOCUMENTS

| | | | | |
|---|---|---|---|---|
| WO | WO 2010063117 A1 * | 6/2010 | | A61F 2/4609 |
| WO | 2011106861 A1 | 9/2011 | | |
| WO | 2012171577 A1 | 12/2012 | | |
| WO | 2012027816 A1 | 3/2013 | | |

OTHER PUBLICATIONS

Cross-product. Dictionary.com. Dictionary.com Unabridged. Random House, Inc. Retrieved from <http://dictionary.reference.com/browse/cross-product> on Jan. 6, 2015.*
Simon, David A., et al. "Development and validation of a navigational guidance system for acetabular implant placement." CVRMed-MRCAS'97. Springer Berlin Heidelberg, 1997. pp. 583-592.*
Widmer, Karl-Heinz. "A simplified method to determine acetabular cup anteversion from plain radiographs." The Journal of arthroplasty 19.3 (2004): 387-390.*

* cited by examiner

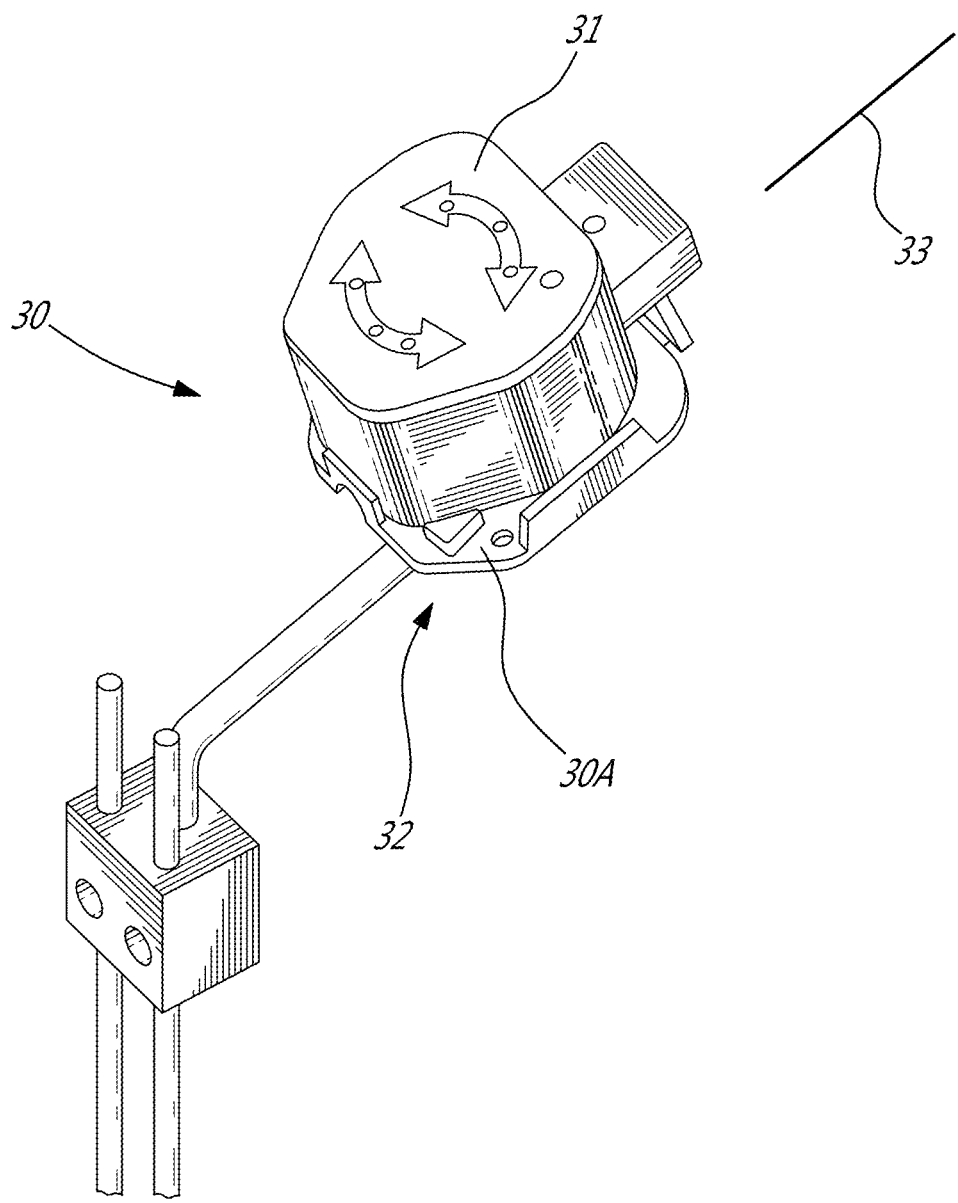
Fig_5

PELVIC DIGITIZER DEVICE WITH INERTIAL SENSOR UNIT AND METHOD

CROSS-REFERENCE TO RELATED APPLICATION(S)

The present application claims priority on U.S. patent application Ser. No. 61/677,104, filed on Jul. 30, 2012, and incorporated herein by reference.

FIELD OF THE APPLICATION

The present application relates to computer-assisted surgery using inertial sensors, and more specifically to the creation of a frame of reference for a pelvis for subsequent navigation of tools using inertial sensors.

BACKGROUND OF THE ART

During orthopedic implant procedures, e.g. total hip replacement (THR), the orientation of the surgical implants has a direct impact on the postoperative function and long term operability of the implant. The conventional surgical techniques use simple "eyeballing" methods or mechanical tools to position the implant. The "eyeballing" method is found to be insufficient to provide an accurate alignment of the implant components with the bones where the implant is attached. The studies have proved that sub-optimally positioned orthopedic implants correlate to improper loading, increased implant wear, and even implant failure.

The current commercially available Computer-Assisted Surgery systems use optical or magnetic tracking systems. These systems are able to track patient coordinate system accurately and reliably. However, the factors, such as high costs, the limited operating range, maintaining a line of sight contact, and magnetic interferences, are main issues associated with these technologies.

The proposed system and method uses self-contained inertial sensors, which do not rely on signal transmission and immune to electromagnetic disturbances. Therefore, it is particularly suitable for the applications in the OR environment containing a large amount of equipment.

SUMMARY OF THE APPLICATION

It is therefore an aim of the present invention to provide a pelvic digitizer device and method for creating a pelvic frame of reference.

Therefore, in accordance with a first embodiment of the present application, there is provided a pelvic digitizer device comprising: a body comprising: a shaft having a tooling end and a handle end with a handle for being manipulated; a visual guide oriented in a reference plane of the digitizer device; a cup connected to the tooling end and adapted to be received in an acetabulum of a patient; and an inertial sensor unit connected to the body, the inertial sensor unit having a preset orientation aligned with the reference plane.

Further in accordance with the first embodiment, the visual guide is a light source adapted to produce a line in the reference plane.

Still further in accordance with the first embodiment, the line and the shaft lie in the reference plane.

Still further in accordance with the first embodiment, the visual guide is a rod connected to the handle.

Still further in accordance with the first embodiment, the rod is generally transverse to the shaft, and the rod and shaft lie in the reference plane.

Still further in accordance with the first embodiment, a receptacle is in the body for releasably receiving the inertial sensor unit in such a way that the preset orientation of the inertial sensor unit is aligned with the reference plane.

Still further in accordance with the first embodiment, the preset orientation of the inertial sensor unit comprises an angle between an acetabulum line and a medio-lateral axis of the patient.

Still further in accordance with the first embodiment, a stopper is adjacent to a rim of the cup, the stopper being adapted to contact a landmark of an acetabular rim.

Still further in accordance with the first embodiment, the preset orientation of the inertial sensor unit has an axis normal to the reference plane.

In accordance with a first embodiment of the present application, there is provided an assembly of a pelvic digitizer device and pelvic tracker device comprising the pelvic digitizer device; and the pelvic tracker device comprising: a tracker body adapted to be fixed to a pelvis of the patient, an inertial sensor unit with a preset orientation, a three DOF rotational joint between in the inertial sensor unit and the body, and a visual guide displaceable with the inertial sensor unit for alignment with the reference plane of the pelvic digitizer device.

Still further in accordance with the second embodiment, a receptacle is in the tracker body for releasably receiving the inertial sensor unit in such a way that the preset orientation of the inertial sensor unit of the pelvic tracker body is aligned with a plane of the receptacle.

In accordance with a first embodiment of the present application, there is provided a method for creating at least part of a pelvic coordinate system of a patient in strict lateral decubitus, comprising: inserting a cup of a pelvic digitizer device in a native acetabulum of the patient; visually aligning a reference plane of the pelvic digitizer device with a frontal plane of the patient, in a visual alignment; and in the visual alignment, initializing an inertial sensor unit of the pelvic digitizer device to set an orientation of the pelvic digitizer device relative to an anterior-posterior axis of the patient.

Still further in accordance with the third embodiment, the cup is aligned with an acetabular rim of the patient while maintaining said visual alignment, and an orientation of the pelvic digitizer device is recorded with the inertial sensor unit to set an orientation of the pelvic digitizer device relative to a medio-lateral axis of the patient using an angle between the acetabular rim and the medio-lateral axis obtained pre-operatively.

Still further in accordance with the third embodiment, the angle used between the acetabular rim and the medio-lateral axis comprises obtaining the angle from a single frontal image of the patient.

Still further in accordance with the third embodiment, an orientation of the pelvic digitizer device is obtained using a cross-product of the medio-lateral axis and the anterior-posterior axis.

Still further in accordance with the third embodiment, inserting a cup comprises installing a cup on a tooling end of the pelvic digitizer device, the cup being selected as a function of a size of the native acetabulum obtained pre-operatively.

Still further in accordance with the third embodiment, visually aligning the reference plane comprises one of aligning a rod and turning on a light source with patient landmarks for visual alignment.

Still further in accordance with the third embodiment, the pelvic coordinate system is transferred to a pelvic tracker device secured to the pelvis.

Still further in accordance with the third embodiment, transferring the pelvic coordinate system comprises align a preset axis of the pelvic tracker device with gravity.

Still further in accordance with the third embodiment, transferring the pelvic coordinate system further comprises aligning a visual guide of the pelvic tracker device with the reference plane.

BRIEF DESCRIPTION OF THE DRAWINGS

FIG. 3A is a perspective view of the pelvic digitizer device with linear light beam relative to a pelvis in accordance with a method of the present disclosure, whereas

FIG. 5 is a perspective view of a tracker device with inertial sensor unit as used with the pelvic digitizer device of FIG. 1.

DESCRIPTION OF THE EXEMPLARY EMBODIMENTS

Figure 1:
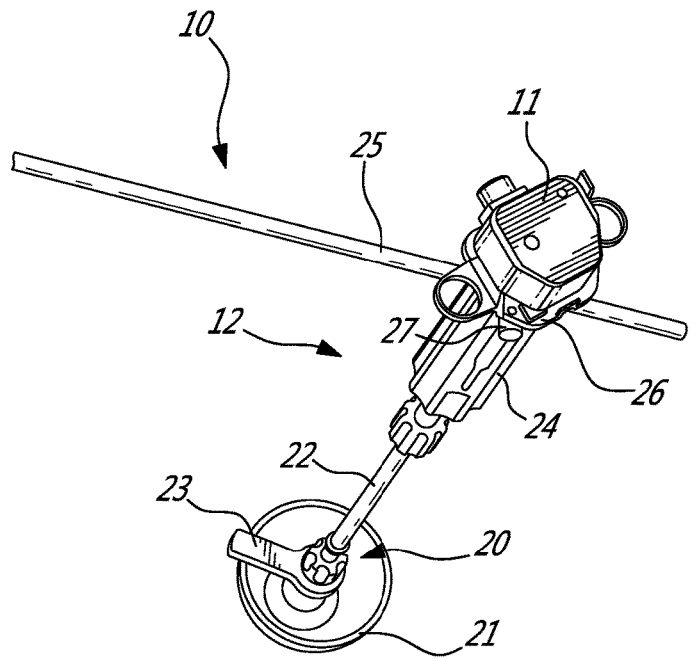
FIG. 1 is a perspective view of a pelvic digitizer device with inertial sensor unit in accordance with an embodiment of the present disclosure.
Figure 2A:
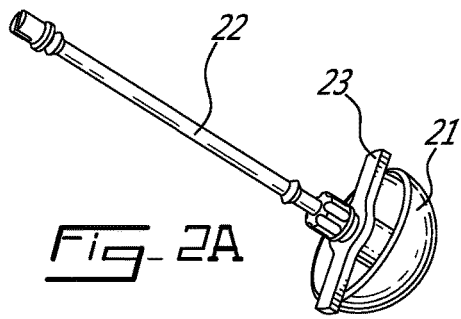
FIGS. 2A to 2D are a series of figures showing variants of a cup and stopper of the pelvic digitizer device of FIG. 1.
Figure 2B:
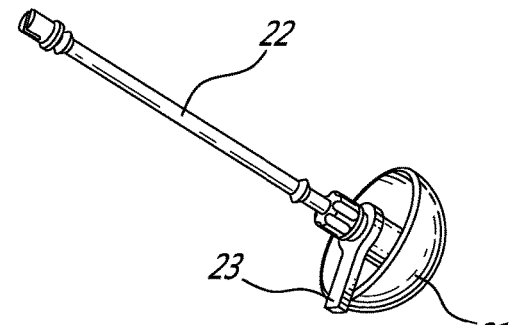
Figure 2C:
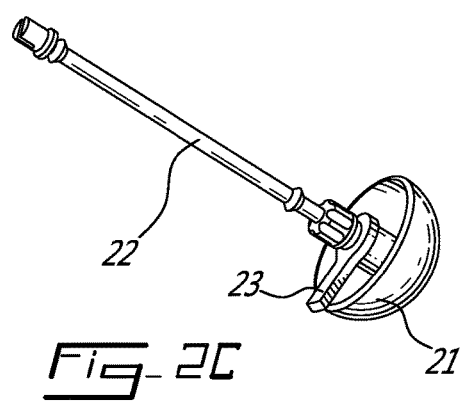
Figure 2D:
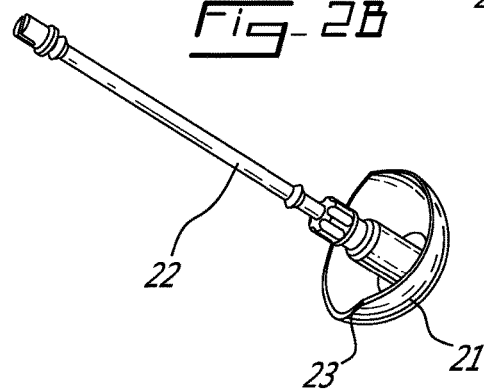

Referring to the drawings and more particularly to FIG. 1, there is a pelvic digitizer device in accordance with the present disclosure at 10. The device 10 is of the type used with an inertial sensor unit 11 mounted on a tool body 12. The inertial sensor unit 11 may be known as a sourceless sensor, a micro-electromechanical sensor unit (MEMS unit), and has any appropriate set of inertial sensors (e.g., accelerometers, gyroscope) to produce tracking data in at least three degrees of rotation (i.e., the orientation about a set of three axes is tracked). The sensor unit 11 may be self enclosed in a pod that is connectable in an accurate and predetermined manner to the tool body 12 of the device 10.

The tool body 12 has a tool end 20 in the shape of a cup 21. The cup 21 is shaped to match the shape of an acetabulum (e.g., a hemisphere or quasi-hemisphere), and the size of the cup 21 may be selected as a function of pre-operative imaging of the acetabulum, as will be described hereinafter. For this purpose, the cup 21 may be releasably connected to a shaft 22 of the tool body 12, such that a cup 21 of appropriate dimension may be selected. A stopper 23 is integral with the cup 21, and may have different configurations as is shown in FIGS. 2A-2D, including a pointy edge. Moreover, the stopper 23 may rotate relative to the shaft 22, to be turned to a desired orientation to contact bone landmarks.

A handle 24 is located at an opposite end of the cup 21 on the shaft 22. The handle 24 is ergonomically configured to be handled by a user. A visual guide 25 is a rod that projects transversally from the handle 24. The visual guide 25 is used to visually guide the user in aligning the device with the body of the patient. In an alternative embodiment, the visual guide 25 is a laser or LED light source that emits a visual line for guidance.

A receptacle 26 is located at the end of the handle 24, and is configured to receive the sensor unit 11 in the accurate and predetermined manner. Alternatively, the sensor unit 11 may be built-in to the tool body 12. However, in both cases, an orientation of the sensor unit 11 is preset relative to the tool body 12, such that tracking about at least one axis (one rotational degree of freedom) is known when the sensor unit 11 is initialized. According to an embodiment, the shaft 22 and the visual guide 25 lie in a plane of the device 10, and the preset orientation of the sensor unit 11 has its axis normal to the plane of the device 10. In other words, when the sensor unit 11 is initialized, for instance by pressing on the button 27, an axis of the sensor unit 11 will be normal to the plane of the device 10 in which the shaft 22 and the visual guide 25 (or light line produced thereby) lie.

Although not shown, the sensor unit 11 may be equipped with visual interfaces to provide data to a user (e.g., LEDs of different colors, such as green and red), or may be connected to a computer-assisted surgery system to transmit the orientation data thereto. The transmission of data may be wireless, in any appropriate protocol (e.g., BLUETOOTH, ZIGBEE, etc).

Now that the device 10 has been described, a method of using the device 10 to create a pelvic frame of reference (a.k.a., pelvic coordinate system) is set forth.

Figure 4:
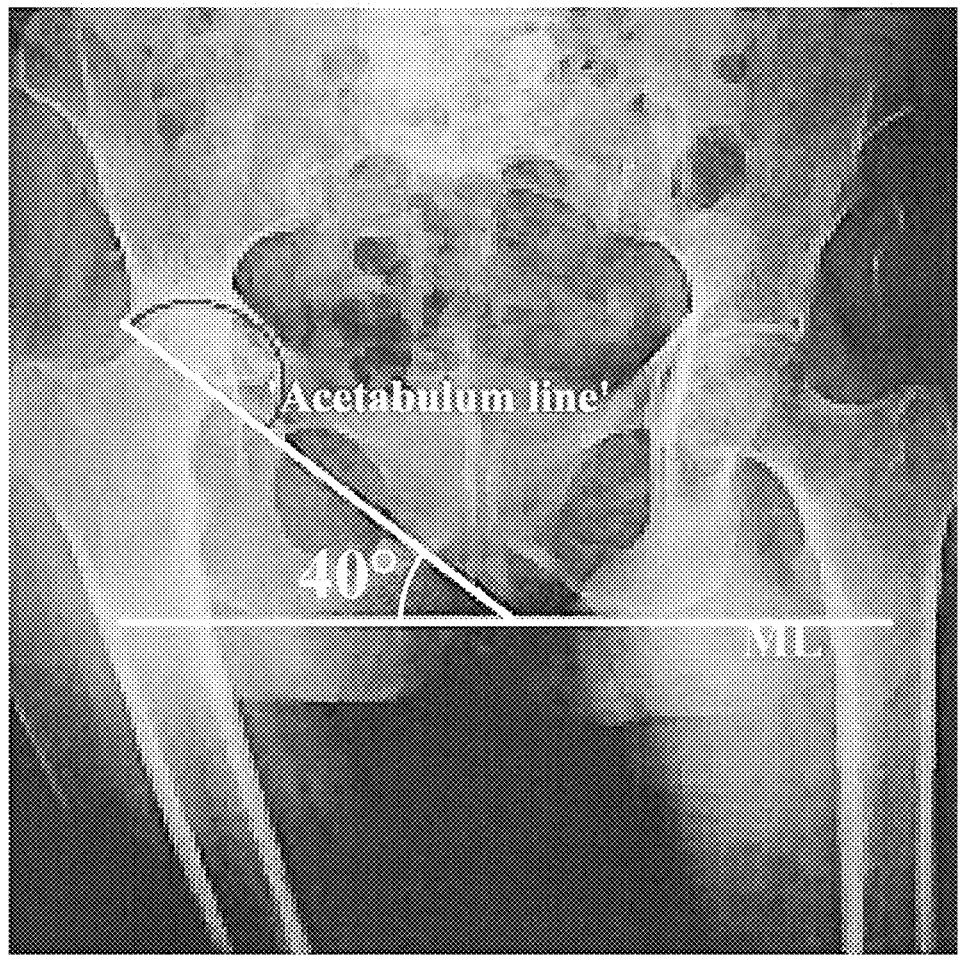
FIG. 4 is a radiographic image of a pelvis showing an angle between acetabulum line and medio-lateral axis.

According to a pre-operative step, the frontal plane of the pelvis of the patient is imaged using any appropriate type of imaging (e.g., X-ray), to obtain an image as in FIG. 4. From this image, angle a may be obtained (shown as 40 degrees), as the acetabulum line, i.e., the line crossing portions of the rim of the acetabulum, relative to the medio-lateral axis (hereinafter ML axis). The ML axis may be the line that connects 2 antero-superior iliac spine (ASIS) points or connects the bottom of two teardrops of the pelvis, as shown in FIG. 4. Also, from the image, the cup size that fits the patient's native acetabulum may be evaluated.

Figure 3A:
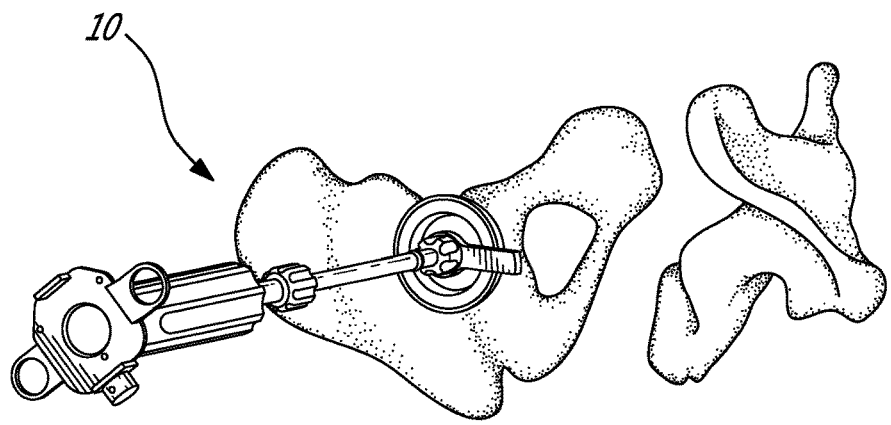
Figure 3B:
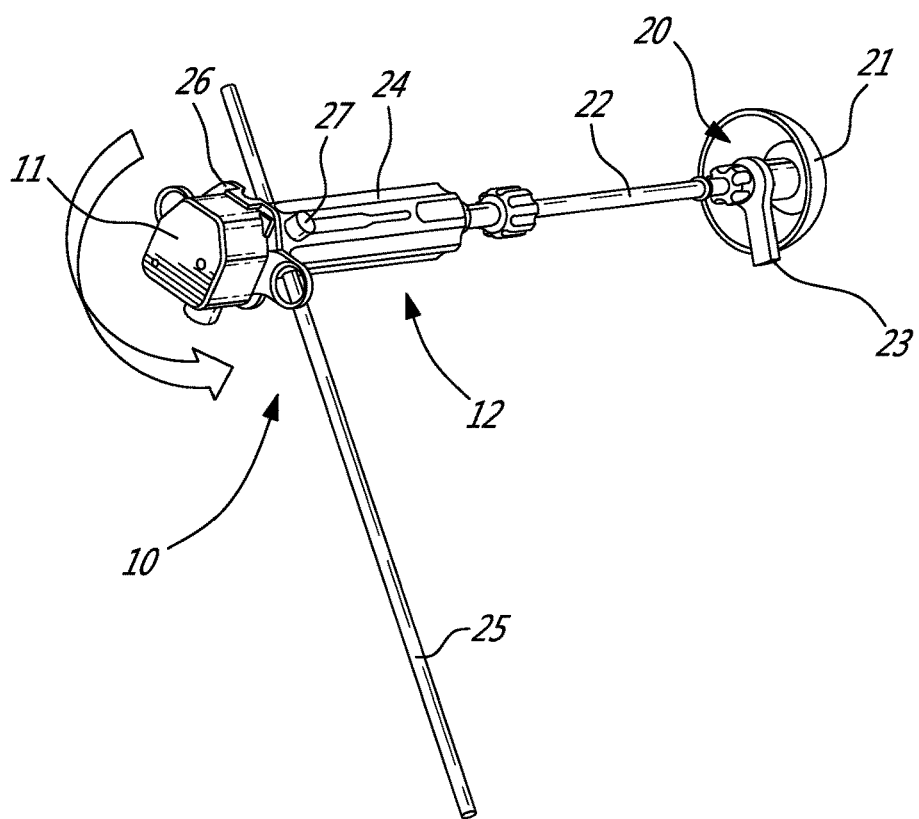
FIG 3B is a perspective view of the pelvic digitizer device with rod.

The next steps are performed intra-operatively, with the device 10 being equipped with a sensor unit 11 with preset orientation and the cup 21 dimensioned to match the pre-operative evaluated size. Referring to FIG. 3, with the patient in a strict lateral decubitus (e.g., with the frontal plane being aligned with gravity) with the frontal plane being perpendicular to the substantially horizontal surface of the operating table, for instance as eyeballed using pelvic landmarks, and with the femur being dislocated from the acetabulum, the cup 21 of the device 10 is inserted in the native acetabulum before it is reamed. The stopper 23 is abutted against the rim of the acetabulum to ensure that the cup 21 is properly inserted in the acetabulum. For example, the device 10 may be waggled back-and-forth in the patient's acetabulum, while keeping the instrument moving in the patient frontal plane. The waggle motion will be stopped by the stopper 23 on the modular cup 21. In the embodiment of the device 10, the stopper 23 points towards the patient's head, but may be configured and rotated to point toward the patient's feet, etc, as a matter of preference of the surgeon, considering the environing soft tissue. The stopper 23 can be adjustable as to where it is located, so that it adapts to the user's preferences. However, there are few bone landmarks, e.g. acetabulum notch, and it is preferred that the stopper 23 cooperates with these landmarks, whereby the orientation of the stopper 23 may be adjusted relative to the shaft 22 to align the stopper 23 with the bone landmarks.

When the stopper 23 contacts the rim of the acetabulum, the visual guide 25 may be visually aligned with the patient's frontal plane. For example, the visual guide 25

(whether a rod as in FIG. 3B or a linear light beam as in FIG. 3A) is pointed towards the patient's head and parallel to the longitudinal axis of the patient. This direction may be arranged to be parallel to the long side of the operating table. The visual guide 25 gives a visual indication to keep the device 10 moving in a plane that is parallel to the patient's frontal plane.

With the visual guide 25 held in such a way that it is generally parallel to the frontal plane of the patient, the sensor unit 11 may be turned on. In the illustrated embodiment, the "on" button 27 is conveniently located on the handle 24. The sensor unit 11 is preset with an orientation, in such a way that orientation about a first rotational degree of freedom is known when the sensor unit 11 is initialized. More specifically, when the sensor unit 11 is turned on, an axis of the sensor unit 11 is normal to the plane of the device 10. As the plane of the device 10 is parallel to the frontal plane of the patient as a result of the steps set forth above on patient positioning and maneuvering of the device 10, the sensor unit 11 has a preset axis aligned with the anterior-posterior (AP) axis of the patient.

The ML axis is then set. As the stopper 23 is stuck on the rim of the acetabulum and the device 10 is maintained parallel to the patient frontal plane, the rim of the modular cup 21 is aligned with the acetabulum line (FIG. 4), the shaft of the acetabulum is perpendicular to rim of the modular cup. At this time, the inertial sensor unit 11 will be able to compute the ML axis based on the preoperatively obtained a angle and the known geometrical relation between the inertial sensor unit 11 and the tool body 12 from the preset instrumental parameters. The computation may be done by rotating the shaft 22 of the device 10, which is known to the inertial sensor unit 12, by 90-alpha degrees. A command must be given to the sensor unit 11 that the ML axis will be set. These rotations will allow the sensor unit 11 to set the ML axis.

Finally, the cranial-caudal (CC) axis is the cross-product of the AP axis and the ML axis. With the three axes set in the manner described above, the device 10 is calibrated as a frame of reference about three rotational axes is created between the device 10 and the pelvis.

As alterations will be made to the acetabulum, the coordinate system must be transferred from the sensor unit 11 on the device 10 to a sensor unit of a tracking device 30, as shown in FIG. 5. The tracking device 30 is secured to the pelvis for instance in the receptacle 30A shown, and has a sensor unit 31 of similar nature and configuration as the sensor unit 11 of the device 10. The inertial sensor unit 31 has a preset orientation for instance with an axis being aligned with a surface of the receptacle 30A, such that the axis is parallel to gravity when the surface of the receptacle 30A is horizontal. According to an embodiment, the tracking device 30 is pinned to the iliac crest. The tracking device 30 is then aligned with the horizon, using the readings from the sensor unit 31. The sensor unit 31 is the equivalent of "bubble" levels being orthogonal to each other. In an embodiment, the sensor unit 31 is connected to a body of the tracking device 30 by a ball joint 32 (or like three rotational DOF joint), to allow such horizontal leveling (and hence for an axis to be parallel to gravity). The various DOFs of the joint 32 may be locked.

With it being level, the sensor unit 31 is rotated around its normal axis to align a visual guide 33 thereof, such as a rod, with the patient's frontal plane, with these rotations being recorded by the sensor unit 31. Accordingly, the tracking device 30 is aligned with the frontal plane, whereby the AP axis is now common to both the devices 10 and 30. In this orientation of the tracking device 30, the pelvic coordinate system may be transferred from the sensor unit 11 of the device 10 to the sensor unit 31 of the tracking device 30. The transfer is performed using the common vectors measured by both sensor units 11 and 31, respectively of the device 10 and the device 30, to build an equation. The common vectors are the AP-axis and gravity. The equation is solved, and the relation between the tracking device 30 and the patient coordinate system of the sensor unit 11 can be found, to complete the pelvis registration.

According to another embodiment, the operating table is rotatable about its transverse axis, i.e., about an axis that is generally normal to the frontal plane of the patient in the strict lateral decubitus. The rotation of the table is used to transfer the pelvic coordinate system from the device 10 to the tracking device 30. To perform such transfer, the device 10 is removed from engagement in the patient's acetabulum. The table is rotated while ensuring that the patient remains generally immovable relative to the table surface. In an embodiment, the OR table is rotated about θ°, remains stable for 15 secs, and then rotated back. While rotating the table, with the tracking device 30 secured to the pelvis of the patient, the readings of the sensor unit 31 are recorded. A tracking device on a table locator, detects the rotation angle (θ) and the rotation axis (r-axis). The expected readings of the device 10 can be mathematically calculated: rotation of tracking device x, y, z axes of the device 10 respectively {around r-axis, with θ°} as if the device 10 was mechanically attached to the pelvis and followed the rotation of the OR table. The patient coordinate system may be transferred from the device 10 to the tracking device 30. The readings of both sensor units 11 and 31 in a first position and second position are used, with the first position being after the calibration of the device 10, and the second position being with the OR table inclined by θ° (using in this case the expected reading for the device 10).

Once the frame of reference of the pelvis is transferred to the pelvic tracking device 30, the pelvis may be tracked in orientation about three rotational degrees of freedom, and this tracking may be used and transferred to tools for instance to determine the anteversion and abduction/adduction angles of these tools. The tools may include reamers, impactors, etc.

The proposed method using the device 10 requires only the patient frontal plane to be aligned with gravity (i.e. the roll angle of the pelvis is required to be zero; however, tilt angle can be arbitrary). Moreover, the proposed method uses only one radiograph, i.e. the frontal plane X-ray. Moreover, the proposed method is a calibration of the devices 10 and 30 performed intra-operatively.

The invention claimed is:
1. A pelvic digitizer device comprising:
a body comprising:
a shaft having a tooling end and a handle end with a handle for being manipulated,
a visual guide oriented in a reference plane of the digitizer device, and
a cup connected to the tooling end and adapted to be received in an acetabulum of a patient; and
an inertial sensor unit connected to the body, the inertial sensor unit having a preset orientation for calibration of the pelvic digitizer device relative to a pelvis of a patient, the preset orientation being based on preoperative imaging specific to the pelvis of the patient, the preset orientation being aligned with the reference plane.

2. The pelvic digitizer device according to claim 1, wherein the visual guide is a light source adapted to produce a line in the reference plane.

3. The pelvic digitizer device according to claim 2, wherein the line and the shaft lie in the reference plane.

4. The pelvic digitizer device according to claim 1, wherein the visual guide is a rod connected to the handle.

5. The pelvic digitizer device according to claim 4, wherein the rod is generally transverse to the shaft, and the rod and shaft lie in the reference plane.

6. The pelvic digitizer device according to claim 1, further comprising a receptacle in the body for releasably receiving the inertial sensor unit in such a way that the preset orientation of the inertial sensor unit is aligned with the reference plane.

7. The pelvic digitizer device according to claim 1, wherein the preset orientation of the inertial sensor unit comprises a preoperatively determined angle between an acetabulum line and a medio-lateral axis of the patient, the preoperatively determined angle being based on the imaging specific to the patient.

8. The pelvic digitizer device according to claim 1, further comprising a stopper adjacent to a rim of the cup, the stopper being adapted to contact a landmark of an acetabular rim.

9. The pelvic digitizer device according to claim 1, wherein the preset orientation of the inertial sensor unit has an axis normal to the reference plane.

10. An assembly of a pelvic digitizer device and pelvic tracker device comprising:
the pelvic digitizer device comprising:
a body comprising:
a shaft having a tooling end and a handle end with a handle for being manipulated,
a visual guide oriented in a reference plane of the digitizer device, and
a cup connected to the tooling end and adapted to be received in an acetabulum of a patient; and
an inertial sensor unit connected to the body, the inertial sensor unit having a preset orientation for calibration of the pelvic digitizer device relative to a pelvis of a patient, the preset orientation being based on pre-operative imaging specific to the pelvis of the patient, the preset orientation being aligned with the reference plane; and
the pelvic tracker device comprising:
a tracker body adapted to be fixed to a pelvis of the patient,
another inertial sensor unit with a preset orientation for calibration of the pelvic tracker device, the preset orientation being based on the pre-operative imaging specific to the pelvis of the patient,
a three DOF rotational joint between the inertial sensor unit and the body, and
a visual guide displaceable with the inertial sensor unit for alignment with the reference plane of the pelvic digitizer device.

11. The assembly according to claim 10, further comprising a receptacle in the tracker body for releasably receiving the inertial sensor unit in such a way that the preset orientation of the inertial sensor unit of the pelvic tracker body is aligned with a plane of the receptacle.

12. A method for creating at least part of a pelvic coordinate system of a patient in strict lateral decubitus, comprising:
obtaining a pelvic digitizer device with an inertial sensor unit programmed with a preset orientation based on pre-operative imaging specific to a pelvis of a patient, the preset orientation being aligned with a reference plane of the pelvic digitizer device;
inserting a cup of a pelvic digitizer device in a native acetabulum of the patient;
visually aligning said reference plane of the pelvic digitizer device with a frontal plane of the patient, in a visual alignment; and
in the visual alignment, initializing an inertial sensor unit of the pelvic digitizer device to set an orientation of the pelvic digitizer device relative to an anterior-posterior axis of the patient.

13. The method according to claim 12, further comprising aligning the cup with an acetabular rim of the patient while maintaining said visual alignment, and recording an orientation of the pelvic digitizer device with the inertial sensor unit to set an orientation of the pelvic digitizer device relative to a medio-lateral axis of the patient using an angle between the acetabular rim and the medio-lateral axis obtained pre-operatively.

14. The method according to claim 13, wherein using the angle between the acetabula rim and the medio-lateral axis comprises obtaining the angle from a single frontal image of the patient.

15. The method according to claim 12, wherein inserting a cup comprises installing a cup on a tooling end of the pelvic digitizer device, the cup being selected as a function of a size of the native acetabulum obtained pre-operatively.

16. The method according to claim 12, wherein visually aligning the reference plane comprises one of aligning a rod and turning on a light source with patient landmarks for visual alignment.

17. The method according to claim 12, further comprising transferring the pelvic coordinate system to a pelvic tracker device secured to the pelvis.

18. The method according to claim 17, wherein transferring the pelvic coordinate system comprises align a preset axis of the pelvic tracker device with gravity.

19. The method according to claim 18, wherein transferring the pelvic coordinate system further comprises aligning a visual guide of the pelvic tracker device with the reference plane.

* * * * *